United States Patent [19]

Okajima et al.

[11] 4,333,957
[45] Jun. 8, 1982

[54] CAPSULE AND PROCESS FOR THE PRODUCTION OF A COLORED GELATIN CAPSULE

[75] Inventors: Yakutaro Okajima, Tokyo; Keiji Sekigawa, Sagamihara, both of Japan

[73] Assignee: Warner-Lambert Company, Morris Plains, N.J.

[21] Appl. No.: 198,992

[22] Filed: Oct. 21, 1980

[51] Int. Cl.$^3$ .............................. A23L 1/00; A23J 3/00
[52] U.S. Cl. ..................................... 426/140; 426/138; 426/250; 426/540; 424/14
[58] Field of Search ............... 426/138, 140, 250, 540, 426/576; 424/14, 15

[56] References Cited

U.S. PATENT DOCUMENTS

| | | | |
|---|---|---|---|
| 2,535,538 | 12/1950 | Koch | 426/250 |
| 3,220,853 | 11/1965 | Golosinec et al. | 426/540 |
| 3,399,803 | 9/1968 | Oglevee | 426/138 |
| 3,620,759 | 11/1971 | Maddox | 426/138 |
| 3,943,262 | 3/1976 | Winkler | 426/250 |

*Primary Examiner*—Jeanette M. Hunter
*Attorney, Agent, or Firm*—Louis S. Gillow

[57] ABSTRACT

A capsule and process for the production of a colored gelatin capsule by homogeneously dispersing in the gelatin carminic acid or laccaic acid and ammonium alum and/or potassium alum, and further incorporating titanium dioxide in the gelatin. Preferably, a gelatin capsule in which the amount of carminic acid or laccaic acid is 0.03 to 0.75% by weight and the amount of ammonium alum and/or potassium alum is 0.01 to 0.25% by weight.

4 Claims, No Drawings

CAPSULE AND PROCESS FOR THE PRODUCTION OF A COLORED GELATIN CAPSULE

SUMMARY AND DETAILED DESCRIPTION

This invention relates to a non toxic, color stable conveniently mass produced gelatin capsule.

Recently, undesirable effects relates to the use of conventional synthetic tar dyes have been discovered. This has intensified society's misgivings about the safety of synthetic tar dyes on the human body.

Natural pigments are used widely as substitutes for synthetic tar dyes in food. A gelatin capsule having beautiful colors and luster, and showing a good stability against heat can be manufactured under practical production conditions by using only a natural pigment selected from carminic acid or laccaic acid or by using the natural pigment in combination with titanium dioxide.

However, the capsules colored by carminic acid or laccaic acid do not exhibit the intended red colors but exhibit violet colors (for example when carminic acid is added thereto, the color is 2.5RP7/4 by modified Munsell notation). The gradations of the colors differs depending upon the amount of pigment added, because carminic acid or laccaic acid interacts with gelatin.

A gelatin capsule prepared in accordance with the present invention has beautiful colors and luster, shows good stability against heat and can be manufactured under practical production conditions. The gelatin capsule is prepared by adding carminic acid or laccaic acid and ammonium alum and/or potassium alum to gelatin or by further adding titanium dioxide thereto.

Carminic acid is found in the body of the female of a variety of the cochineal insect (*Coccus cacti, L.*) which is parasitic to a cactus growing wild in a desert area of Central and South America and is obtained therefrom as a dark-red powder by extraction and purification. It is permitted as a coloring agent for food in the United States and in European countries. Carminic acid is also described in the "Merck Index," 9th edition, page 235, Merck & Co., Inc. (1976).

Laccaic acid is a red natural dye obtained by extraction and purification from Stick Lac growing in South East Asia, and has been used for the same purpose as that of carminic acid.

Ammonium alum is used widely as a color retaining agent for pickles and cooked foods, and as an baking powder. It also is used for purification of drinking water and as a dyestuff.

Potassium alum is used for the same purposes as ammonium alum in the food industry and is also used in pharmaceuticals.

The object of this invention can be achieved by using titanium dioxide as a powder.

Ammonium alum and/or potassium alum may be used to retain the red color of carminic acid or of laccaic and they may be added in an optional order. For example:

1. An aqueous solution of carminic acid or laccaic acid and ammonium alum and/or potassium alum is added to an original solution of gelatin for producing a gelatin capsule;
2. Ammonium alum and/or potassium alum is added to a gelatin solution colored previously by carminic acid or laccaic acid;
3. Carminic acid or laccaic acid is added to a gelatin solution containing ammonium alum and/or potassium alum.

Titanium dioxide may further be added to an original solution of gelatin in an optional order and dispersed homogeneously therein. For example:

1. Carminic acid or laccaic acid and ammonium alum and/or potassium alum are added to a gelatin solution into which titanium dioxide is dispersed homogeneously;
2. Titanium dioxide is dispersed in a gelatin solution colored by carminic acid or laccaic acid and ammonium alum and/or potassium alum; etc.

A gelatin solution as used in this invention may be prepared by dissolving gelatin in hot water, and adding a preservative thereto as occasion demands. The concentration of the gelatin solution is about 35% by weight and the viscosity of the solution ranges from 800 to 1000 cps at 45° C. A special device is not required for homogeneous dispersion of the additives. It is sufficient to disperse them with known devices.

The object of this invention may also be attained by using in combination plasticizers, preservatives, dispersing agents and other additives necessary for manufacturing a gelatin capsule.

Further the capsules which are formed and processed according to this invention exhibit a red color which is stable to temperature and light.

The color of the capsule can be varied continuously depending upon the amounts of carminic acid or laccaic acid and titanium dioxide used.

A capsule colored by carminic acid or laccaic acid together with ammonium alum and/or potassium alum according to this invention is non toxic. It shows the same dissolution characteristics as conventional capsules when tested in accordance with the Dissolution Test in the United States Pharmacopoeia. Therefore, such a capsule can be used for pharmaceuticals and for food.

The present invention will further be explained in more detail by the following Examples which, however, should not be construed to limit the invention.

EXAMPLE 1

Gelatin was dissolved in hot water and a preservative was added thereto to prepare a gelatin solution having a concentration of 35% by weight and a viscosity of 900 cps at 45° C.

To the original solution of gelatin were added an aqueous solution of carminic acid and an aqueous solution of ammonium alum. The resultant mixture was homogenized. The amounts of carminic acid and ammonium alum added to gelatin are shown in Table 1. Hard gelatin capsules were formed on conventional equipment using the mixture. The capsules thus obtained were transparent and exhibited various red colors of high quality. The amount of ammonium alum added was 0.2–10 mole per one mole of carminic acid.

TABLE 1

| STABILITY AND COLOR | | | | |
|---|---|---|---|---|
| Carminic acid (wt. %) | Ammonium alum (wt. %) | Color | 40° C. × 40%-RH × 4 weeks | 2.5KW - Xenon lamp, 6 hours |
| 0.03 | 0.01 | 2.5RP6/8 | no change | no change |
| 0.09 | 0.03 | 2.5RP5/10 | " | " |
| 0.15 | 0.05 | 2.5RP5/12 | " | " |
| 0.21 | 0.07 | 2.5RP6/12 | " | " |

TABLE 1-continued

STABILITY AND COLOR

| Carminic acid (wt. %) | Ammonium alum (wt. %) | Color | 40° C. × 40%-RH × 4 weeks | 2.5KW - Xenon lamp, 6 hours |
|---|---|---|---|---|
| 0.30 | 0.10 | 2.5R 4/14 | " | " |
| 0.75 | 0.25 | 2.5R 4/14 | " | " |

Carminic acid: Sanei Chemical Co., Ltd.
Color: according to modified Munsell notation (JIS Z-8721)

As is clear from Table 1, the capsules colored by carminic acid and ammonium alum were stable to light and the passage of time.

EXAMPLE 2

Capsules colored by carminic acid and ammonium alum were formed in the same manner as in Example 1 except that titanium dioxide was used in combination. The amounts of carminic acid, ammonium alum and titanium dioxide added are shown in Table 2. The capsules thus obtained exhibited red colors and were opaque.

TABLE 2

STABILITY AND COLOR

| Carminic acid (wt. %) | Ammonium alum (wt. %) | Titanium dioxide (wt. %) | Color | 40° C. × 40%-RH × 4 weeks | 2.5KW- Xenon lamp, 6 hours |
|---|---|---|---|---|---|
| 0.03 | 0.01 | 1.5 | 5RP7/8 | no change | no change |
| 0.09 | 0.03 | 1.5 | 5RP6/10 | " | " |
| 0.15 | 0.05 | 1.5 | 7.5RP5/12 | " | " |
| 0.21 | 0.07 | 1.5 | 7.5RP5/12 | " | " |
| 0.30 | 0.10 | 1.5 | 10RP4/14 | " | " |
| 0.75 | 0.25 | 1.5 | 7.5RP4/14 | " | " |

As is clear from Table 2, the capsules colored by using carminic acid, ammonium alum and titanium dioxide were stable to light and the passage of time.

EXAMPLE 3

Hard gelatin capsules were formed by using an aqueous solution of carminic acid and potassium alum in the same manner as in Example 1. The amounts of carminic acid and potassium alum added to gelatin are shown in Table 3. The capsules thus obtained exhibited various red colors and were transparent. Sufficient effect was observed by using 0.2 mole of potassium alum per one mole of carminic acid. The capsules exhibited good colors similar to the capsules containing ammonium alum.

TABLE 3

STABILITY AND COLOR

| Carminic acid (wt. %) | Potassium alum (wt. %) | Color | 40° C. × 40%-RH × 4 weeks | 2.5 KW - Xenon lamp, 6 hours |
|---|---|---|---|---|
| 0.03 | 0.01 | 2.5RP6/8 | no change | no change |
| 0.09 | 0.03 | 2.5RP6/10 | " | " |
| 0.15 | 0.05 | 2.5RP5/12 | " | " |
| 0.21 | 0.07 | 2.5RP6/12 | " | " |
| 0.30 | 0.10 | 2.5R 4/14 | " | " |
| 0.75 | 0.25 | 2.5R 4/14 | " | " |

As is clear from Table 3, the capsules colored by using carminic acid and potassium alum were stable to light and the passage of time.

EXAMPLE 4

Capsules colored by carminic acid and potassium alum were formed in the same manner as in Example 1 except that titanium dioxide was homogeneously mixed therein. The amounts of carminic acid, potassium alum and titanium dioxide added are shown in Table 4. The capsule thus obtained exhibited various red colors and were opaque.

TABLE 4

STABILITY AND COLOR

| Carminic acid (wt. %) | Potassium alum (wt. %) | Titanium dioxide (wt. %) | Color | 40° C. × 40%-RH × 4 weeks | 2.5KW-Xenon lamp, 6 hours |
|---|---|---|---|---|---|
| 0.03 | 0.01 | 1.5 | 5RP7/8 | no change | no change |
| 0.09 | 0.03 | 1.5 | 5RP6/10 | " | " |
| 0.15 | 0.05 | 1.5 | 7.5RP5/12 | " | " |
| 0.21 | 0.07 | 1.5 | 7.5RP5/12 | " | " |
| 0.30 | 0.10 | 1.5 | 10RP4/14 | " | " |
| 0.75 | 0.25 | 1.5 | 7.5RP4/14 | " | " |

As is clear from Table 4, the capsules colored by using carminic acid, potassium alum and titanium dioxide were stable to light and the passage of time.

EXAMPLE 5

To a viscosity-regulated original solution of gelatin were added an aqueous solution of laccaic acid and ammonium alum. The resultant mixture was homogenized. The amounts of laccaic acid and ammonium alum added to gelatin are shown in Table 5. Hard gelatin capsules were formed on conventional equipment using the mixture. The capsules thus obtained exhibited various red colors and were transparent. Sufficient effect was observed by using 0.2 mole of ammonium alum per one mole of laccaic acid.

TABLE 5

STABILITY AND COLOR

| Laccaic acid (wt. %) | Ammonium alum (wt. %) | Color | 40° C. × 40%-RH × 4 weeks | 2.5KW-Xenon lamp, 6 hours |
|---|---|---|---|---|
| 0.03 | 0.01 | 2.5RP8/4 | no change | no change |
| 0.09 | 0.03 | 2.5RP6/8 | " | " |
| 0.15 | 0.05 | 2.5RP5/12 | " | " |
| 0.21 | 0.07 | 5RP4/12 | " | " |
| 0.30 | 0.10 | 7.5RP4/14 | " | " |

As is clear from Table 5, the capsules colored by using laccaic acid and ammonium alum were stable to light and the passage of time.

EXAMPLE 6

Capsules colored by using laccaic acid and ammonium alum were formed in the same manner as in Example 5 except that titanium dioxide was further mixed homogeneously therein. The amounts of laccaic acid, ammonium alum and titanium dioxide added are shown in Table 6. The capsules thus obtained exhibited various red colors and were opaque.

TABLE 6

STABILITY AND COLOR

| Laccaic acid (wt. %) | Ammonium alum (wt. %) | Titanium dioxide (wt. %) | Color | 40° C. × 40%-RH × 4 weeks | 2.5KW-Xenon lamp, 6 hours |
|---|---|---|---|---|---|
| 0.03 | 0.01 | 1.5 | 2.5RP7/6 | no change | no change |
| 0.09 | 0.03 | 1.5 | 5RP5/10 | " | " |
| 0.15 | 0.05 | 1.5 | 2.5RP5/10 | " | " |
| 0.21 | 0.07 | 1.5 | 5RP4/10 | " | " |
| 0.30 | 0.10 | 1.5 | 5RP4/10 | " | " |

As is clear from Table 6, the capsules colored by using laccaic acid, ammonium alum and titanium dioxide were stable to light and the passage of time.

We claim:

1. A process for coloring gelatin used for forming gelatin capsules comprising: a. homogeneously dispersing carminic acid or laccaic acid and ammonium alum and/or potassium alum in the gelatin, and b. forming gelatin capsules from the resulting gelatin dispersion.

2. A gelatin capsule made by the process according to claim 1 wherein the amount of carminic acid or laccaic acid is 0.03–0.75% by weight and the amount of ammonium alum and/or potassium alum is 0.01–0.25% by weight.

3. A process according to claim 1 wherein titanium dioxide is further added to said gelatin dispersion in step a.

4. A gelatin capsule made by the process according to claim 3 wherein the amount of titanium dioxide is 0.1–3.0% by weight.

* * * * *